Figure 1:
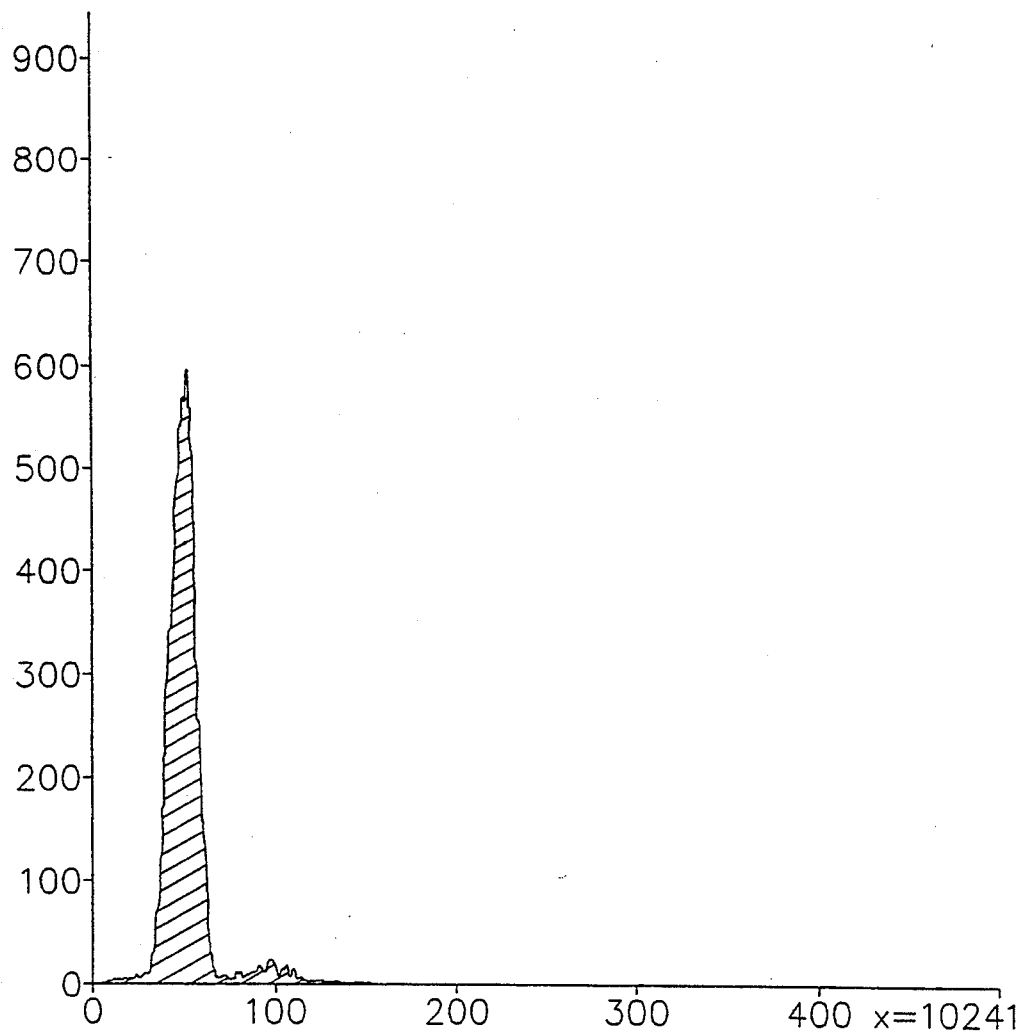
Figure 2:
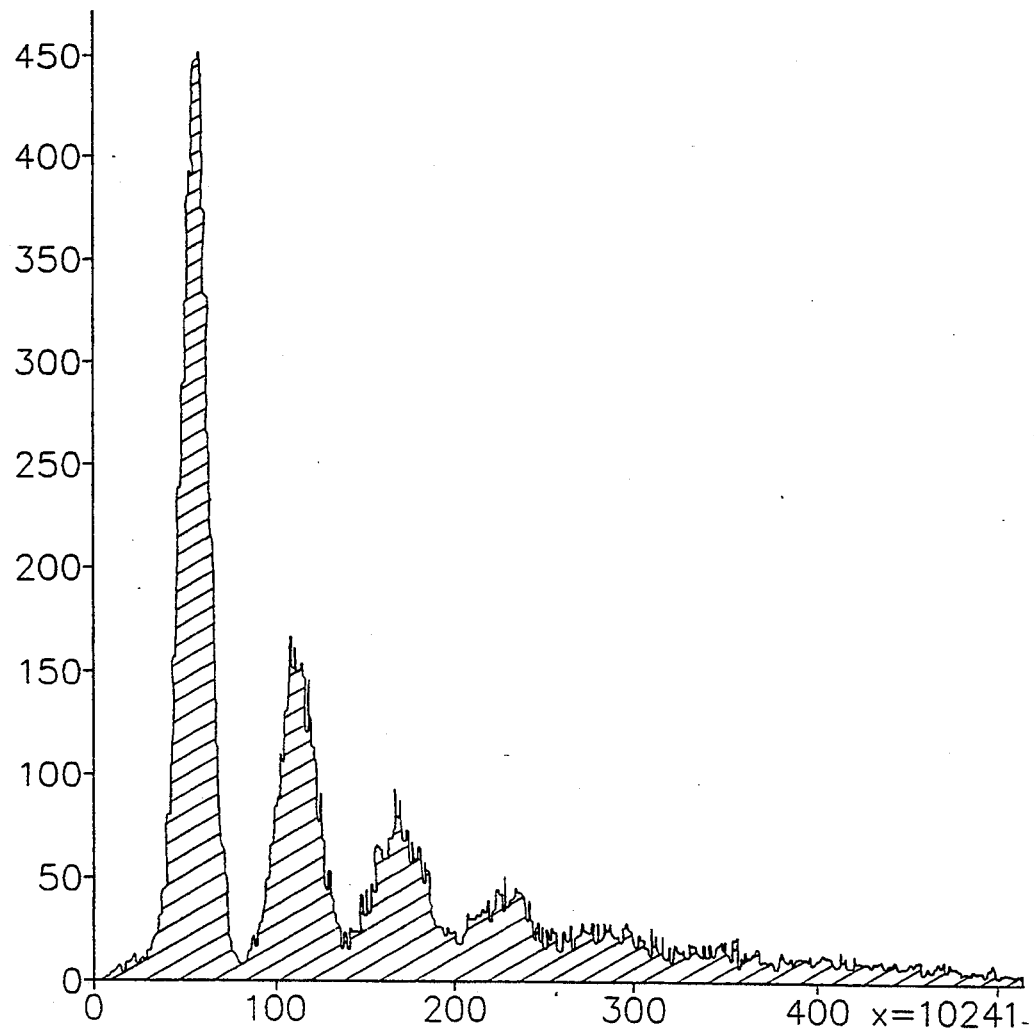

United States Patent [19]

Van Hoegaerden

[11] Patent Number: 5,405,784
[45] Date of Patent: Apr. 11, 1995

[54] AGGLUTINATION METHOD FOR THE DETERMINATION OF MULTIPLE LIGANDS

[75] Inventor: Michel Van Hoegaerden, Mormant, France

[73] Assignee: Chemunex, Maisons Alfort, France

[21] Appl. No.: 22,321

[22] Filed: Feb. 25, 1993

Related U.S. Application Data

[63] Continuation of Ser. No. 499,509, Aug. 3, 1990, Pat. No. 5,219,763.

[30] Foreign Application Priority Data

Nov. 4, 1988 [FR] France .................. 88 14420

[51] Int. Cl.⁶ .................. G01N 33/538; G01N 33/546
[52] U.S. Cl. ........................ 436/523; 356/441; 356/442; 435/973; 436/172; 436/531; 436/533; 436/534; 436/541; 436/805
[58] Field of Search ............ 422/73, 82.08; 435/973; 436/164, 172, 514, 519, 523, 531, 533, 534, 541, 800, 805; 356/335, 441, 442

[56] References Cited

U.S. PATENT DOCUMENTS

| | | | |
|---|---|---|---|
| 4,499,052 | 2/1985 | Fulwyler | 422/82.08 |
| 4,550,017 | 10/1985 | Liu et al. | 436/520 |
| 4,564,598 | 1/1986 | Briggs | 436/172 |
| 4,717,655 | 1/1988 | Fulwyler | 436/534 |
| 4,745,075 | 5/1988 | Hadfield et al. | 436/531 |
| 4,829,011 | 5/1989 | Gibbons | 436/533 |
| 4,837,168 | 6/1989 | de Jaeger et al. | 436/800 |
| 4,918,004 | 4/1990 | Schwartz | 436/800 |
| 4,934,811 | 6/1990 | Watts et al. | 356/73 |
| 4,960,715 | 10/1990 | Hadfield et al. | 436/534 |
| 5,047,321 | 9/1991 | Loken et al. | 435/973 |

FOREIGN PATENT DOCUMENTS

| | | |
|---|---|---|
| 126450 | 11/1984 | European Pat. Off. . |
| 2627286 | 8/1989 | France . |
| 3811566 | 10/1988 | Germany . |

OTHER PUBLICATIONS

Patent Abstracts of Japan, vol. 10, No. 322, Oct. 31, 1986, p. 511, JP-A-61 128169, Jun. 16, 1986, Mitsubishi Chem. Ind. Ltd.

Biological Abstracts, vol. 82, No. 5, 1986, P. K. Bjornsen: "Automatic Determination of Bacterioplankton Biomass by Image Analysis", p. AB-574, Abstract 45417.

*Primary Examiner*—David Saunders
*Assistant Examiner*—Christopher L. Chin
*Attorney, Agent, or Firm*—Bell, Seltzer, Park & Gibson

[57] ABSTRACT

The invention provides a method capable of determining the presence or absence of each of a plurality of different ligands in a specimen. The specimen is contacted with a predetermined number of different homogeneous populations of fluorescence beads having one or more predetermined antiligands affixed to their surface. The specimen and bead mixture is analyzed using a means having a single parameter for measuring the fluorescence per ligand to determine the number of nonagglutinated beads, the number of agglutinated beads, the number of bead aggregates, and for each aggregate, the number of beads it comprises. This information is used to correlate the presence or absence in the specimen of each of the different ligands analyzed for. The method of the invention thus provides for the simultaneous determination of a predetermined number of ligands in a specimen using only a single bead contacting step.

14 Claims, 3 Drawing Sheets

AGGLUTINATION METHOD FOR THE DETERMINATION OF MULTIPLE LIGANDS

This application is a continuation of application Ser. No. 07/499,509, filed Aug. 3, 1990, U.S. Pat. No. 5,219,763.

The present invention relates to a process for accurately and specifically determining in a liquid or semi-liquid, at least one biological, organic or drug soluble substance, even if it is present in extremely small amounts by means of a suitable agglutination reaction.

It is known to detect and to determine soluble substances and particularly peptides or proteins by an agglutination reaction or an agglutination inhibition reaction.

The agglutination reaction is the direct consequence of the fixation of a agglutinating antibody on a cell, for example, and thus calls for antigen-antibody complexes or hormone receptor complexes having agglutinating properties.

Nonetheless, it should be recalled that although these reactions may be easy to produce, their interpretation by the naked eye is mostly delicate and requires the presence of a large amount of substance to be assayed in the specimen, for interpretation to be easy.

An agglutination reaction can be contemplated in various biological contexts; in particular in the field of immunology, agglutination is the manifestation of the formation of a complex.

There exist so-called direct methods (antigen/antibody complex), so-called indirect methods or methods of inhibition by competition; there are also known assay methods of the so-called "sandwich" or bisite type; in these "sandwich" type methods, two antibodies are used, one to capture the antigen, the other to reveal its presence, if this antigen is in fact present and has been captured by the first antibody. Generally, the first antibody is fixed to a solid support (plate, bead . . . ), the second antibody being conjugated with a reaction "developer" such as fluorochrome, radio-isotope, or enzyme.

In an agglutination reaction, red blood cells coated with an antigen serve for detecting corresponding specific antibodies (hemagglutination). An extension of the agglutination methods has consisted of using plastic beads: in the case of a positive reaction, the appearance of a macroscopic "granulation" (passive agglutination) is observed. A reverse procedure has also been described: the antibodies are fixed to beads and serve to detect the corresponding antigens. The sensitivity of such a method is high, but, as has already been mentioned above, the interpretation of the result is not objective and is variable as a function of the observer, the amount of agglutination being a function of the amount of antigen present for a certain range of concentrations of this antigen.

In order to overcome this drawback of agglutination methods and in order to make them quantitative, a certain number of authors have proposed the counting of the non-agglutinated particles by means of a suitable particle counter especially a blood cell counter.

MASSON et al (Particle Counting Immunoassay, Meth. Enzymol., 1981, 74, 106-139) propose a method of determining various antigens (proteins, peptides . . . ), antibodies, haptens and immunocomplexes by means of an agglutination reaction between latex particles 0.8 $\mu$m in diameter coated with antibodies or suitable antigens and said antigens or antibodies or haptens or immunocomplexes, and the counting of the non-agglutinated particles by means of a particle counter, particularly a red blood cell counter which is a small angle defracted light detector. The counting of the non-agglutinated particles enables evaluation of the extent of the agglutination reaction and, consequently, the amount of product to be determined.

The detector is parametered so as to take no account electronically of particles whose diameter is less than 0.6 $\mu$m and particles whose diameter is greater than 1.2 $\mu$m (agglutinated particles).

MASSON described various elements of this method in a certain number of patents:

U.S. Pat. No. 4,062,935 (1977), claims a method of detecting antigen/antibody complexes which comprises the addition to the sample of a rheumatoid factor (RF) and material which agglutinates RF on contact, then detection of the amount of agglutination of said material compared with a standard mixture of said material and of RF; said material is constituted by inert particles coated with immunoglobulins, said particles being, more particularly, of polystyrene. This patent also describes a method of detection of the presence or the absence in a specimen of biological fluid of antibody/antigen complexes comprising the addition to the sample of a known amount of RF and a known amount of latex particles coated with IgG's characterised in that the RF is bound to any antigen/antibody complex present, the remainder of the RF entraining the agglutination of latex particles; then determination of the amount of said RF remainder by counting agglutinated latex particles and comparison of the result with a standard graph.

U.S. Pat. No. 4,138,213 (1979) describes an automated method of determining a quantity of an antibody or an antigen in a biological fluid specimen, comprising several steps and particularly a step of counting the number of non-agglutinated particles.

U.S. Pat. No. 4,162,895 (1979) describes a method of detecting antigens, antibodies or antigen/antibody complexes, which employs a reaction based on mouse serum; this reagent is combined only with antigen/antibody complexes and is used within the scope of agglutination reactions, for example a method of detecting antibodies which comprises the addition to the specimen of a known amount of particles coated with antigens corresponding to said antibodies then counting the number of non-agglutinated particles and calculation of the amount of antibodies present in the specimen.

U.S. Pat. No. 4,184,849 (1980) describes a method of detecting antigens and antibodies in a liquid specimen by employing a suitable agglutination reaction and detection of the extent of the agglutination, which permits determination of the amount of antibodies or of antigens present in the specimen; into the liquid are introduced two reagents in the form of particles which agglutinate together but whose agglutination is inhibited by antibodies or antigens possibly present.

U.S. Pat. No. 4,397,960 (1983) describes an assay method for an antigen by an agglutination reaction. The assay consists of the determination of the extent of agglutination of latex particles in the solution and thus permits the determination of the amount of antigen in the specimen; the estimation of the agglutination is performed by selective counting of the agglutinated and non-agglutinated latex particles.

These various methods have nonetheless a certain number of drawbacks:

it is necessary to treat the specimen so as to remove any particle which could constitute a false positive; to do this, it is necessary to subject the specimen to a certain number of physical or chemical operations such as the use of particular buffers, filtration, centrifugation;

the numbering of the agglutinated particles is only possible in clear media;

besides, counting by small angle defraction does not permit good sensitivity if it attempts to count agglutinated particles (unseparated peaks and hence difficult to interpret);

in addition, they do not permit the simultaneous detection of several ligands.

Applicant consequently made it an object to provide a method not having the drawbacks of the agglutination methods described in the prior art.

By antiligand is meant a molecular structure capable of recognizing and binding specifically to the one or more organic, biological or medicinal substances to be sought, called below ligands.

It is an object of the present invention to provide a specific method of detecting and/or of determining one or several ligands to be analyzed in a liquid, semi-liquid or pasty specimen, by a direct, indirect agglutination method or agglutination inhibition method, by competition, by employing fluorescent structures, called below beads, adapted to fix a suitable antiligand, which method is characterized in that the specimen to be analyzed is contacted with a single homogeneous population of beads per ligand up to two ligands to be detected and less than one population of beads per ligand for three ligands and more to be detected and wherein there is detected and/or counted simultaneously the number of non-agglutinated beads, the number of agglutinated beads, the number of bead aggregates, and for each aggregate, the number of beads that it comprises, using measuring means with a single parameter of measuring fluorescence per ligand, said method enabling, by the single contacting, the detection and/or the determination of several ligands simultaneously.

By homogeneous population of fluorescent beads, is meant a collection of identical beads, that is to say whose fluorochrome emission wavelength, diameter and/or density are identical, as well as the one or more antiligands fixed to their surface.

According to an advantageous embodiment of the method according to the invention, said beads comprise at least two antiligands fixed to their surface.

According to another advantageous embodiment of the method according to the invention, said beads have a diameter comprised between 0.05 $\mu$m and 10.0 $\mu$m.

The fluorescent beads according to the detection system can be, particularly, latex beads, polyacrylamide beads, cellulose beads, polystyrene beads, agarose beads, PVC beads or glass beads.

According to yet another advantageous embodiment of the method according to the invention, the one or more antiligands are selected from the group which comprises antigens, antibodies, receptors, lectins, proteins for fixation to immunoglobulins of type A or G and avidines, specific to the one or more substances or ligands to be sought.

According to an advantageous feature of this embodiment, the antibodies are monoclonal antibodies.

According to another advantageous feature of this embodiment, the antibodies are polyclonal antibodies.

The total amount of fluorescent lights and defracted lights vary as a function of the number of agglutinated beads in each agregate or agglutinate and thus enable, using detection means for fluorescent and/or defracted light, the discrimination of the number of fluorescent beads present in each agglutinate and of their size.

Such discrimination enables the number of doublets, triplets, quadruplets etc., formed to be known and gives, for this reason, to this method of determination, a sensitivity and a precision of measurement which are distinctly increased.

The substances to be analyzed which can particularly be detected by the method according to the invention, are all ligands capable of fixing an antiligand, for example organic, biological or medicinal substances and especially antigens, antibodies, haptens and immuno-complexes, hormones, membranal receptors, lectins, proteins of the type A or G or avidines.

In yet another embodiment of the method according to the invention, the fluorescence measuring means is selected from the group which comprises the flow cytometer, the image analyzer and a laser sweep system.

The method of detection and of counting according to the invention, has a certain number of advantages both economic (little manipulation, very fast counting time) and technical:

it permits, particularly, the counting of agglutinated and non-agglutinated beads in a turbid or viscous medium;

it permits the counting of agglutinated and non-agglutinated beads almost singly;

it is, for this reason, very sensitive, which enables the determination of very small amounts of a desired substance;

the fluorescent beads used avoid interference with other particles possibly present and oblige neither a physical separation of particles possibly present in the specimen to be assayed nor washing steps, which constitutes a homogeneous assay; in fact, the use of the detection system according to the invention permits working in a complex medium containing a large mass of other particles, the number of self-fluorescent elements being lower and can be ignored by the detection means, especially by a judicious choice of optical filters;

it enables discrimination of non-agglutinated beads, doublets, triplets, etc . . . , since it permits an absolute measurement of the intensity and the fluoresence wave-length of each particle or aggregate of particles, one by one.

it is possible, especially, and this, without this being limiting, to use the flow cytometer described in French Patent application no. 88 02937: it permits the handling of specimens of considerable volume, possesses an automatic washing system between each sample, and is designed for routine use; it is, in addition, capable of detecting each agglutinated or non-agglutinated bead and of counting them individually, up to a frequency of 3,000 per second.

The form of the flow cell is selected to reduce to their minimum hydrodynamic extraction forces.

It is in addition an object of the present invention to provide a kit or outfit ready-for-use for practising the detection and/or assay method according to the invention, characterized in that it comprises at least one population of beads on which is fixed at least one suitable antiligand, possibly associated with suitable buffers.

According to an advantageous embodiment of the kit according to the invention, it comprises at least one bead population, on which are fixed at least two suitable different antiligands.

In another advantageous embodiment of the kit according to the invention, it comprises different populations of beads in admixture.

Besides the foregoing features, the invention comprises yet other features which will emerge from the description which follows, which refers to examples of practising the method according to the invention.

It must be well-understood, however, that these examples are given purely by way of illustration of the invention, of which they do not constitute in any way a limitation.

The method according to the invention comprises the formation of complexes by contact of the specimen with fluorescent beads on which is fixed at least one suitable antiligand, under conditions suitable for the appearance of an agglutination or for the inhibition of an agglutination, and then the detection of the agglutinated and non-agglutinated beads.

In a preferred embodiment of the method, populations of fluorescent beads bearing complementary antiligands of the ligand to be assayed are mixed in equal number, about 50,000 per ml. The solution or suspension to be tested is added in a volume which can vary from 3 to 1,000 µl or more. An incubation of 37° C. accelerates the formation of the ligand-antiligand bond; the duration of this incubation depends essentially on the affinity constant of the antiligands employed; the final sensitivity of the test also will depend thereon.

The method according to the invention, permits the detection of a single fluorescent bead. If two of them are counted, it is possible simultaneously to determine if they are separated or agglutinated, and in the case where they are agglutinated, if they have the same characteristics or not. The sensitivity of this method thus enables, theoretically, measurement of the presence of a single ligand molecule, if the latter succeeds in agglutinating two fluorescent beads, of the same spectral characteristics or not.

In another advantageous embodiment of the method, the measurement of a concentration of small molecules, to which two antiligands could not be fixed is also possible: the fixation of the ligand (haptens) or of a derivative of the latter on a bead population of the specific antiligand on another bead population enables the performance of a test in competition in which the agglutination of the beads is inhibited by the free hapten or a derivative of the latter, possibly present to be assayed.

EXAMPLE 1

Detection of enterotoxin A (A-type protein) of *Staphylococcus aureus* by the method according to the invention 1) Preparation of fluorescent beads coated with an antiligand (detection system)

In a first phase, the detection system is prepared by coupling fluorescent particles with the appropriate reagent by known methods.

Figure 3:
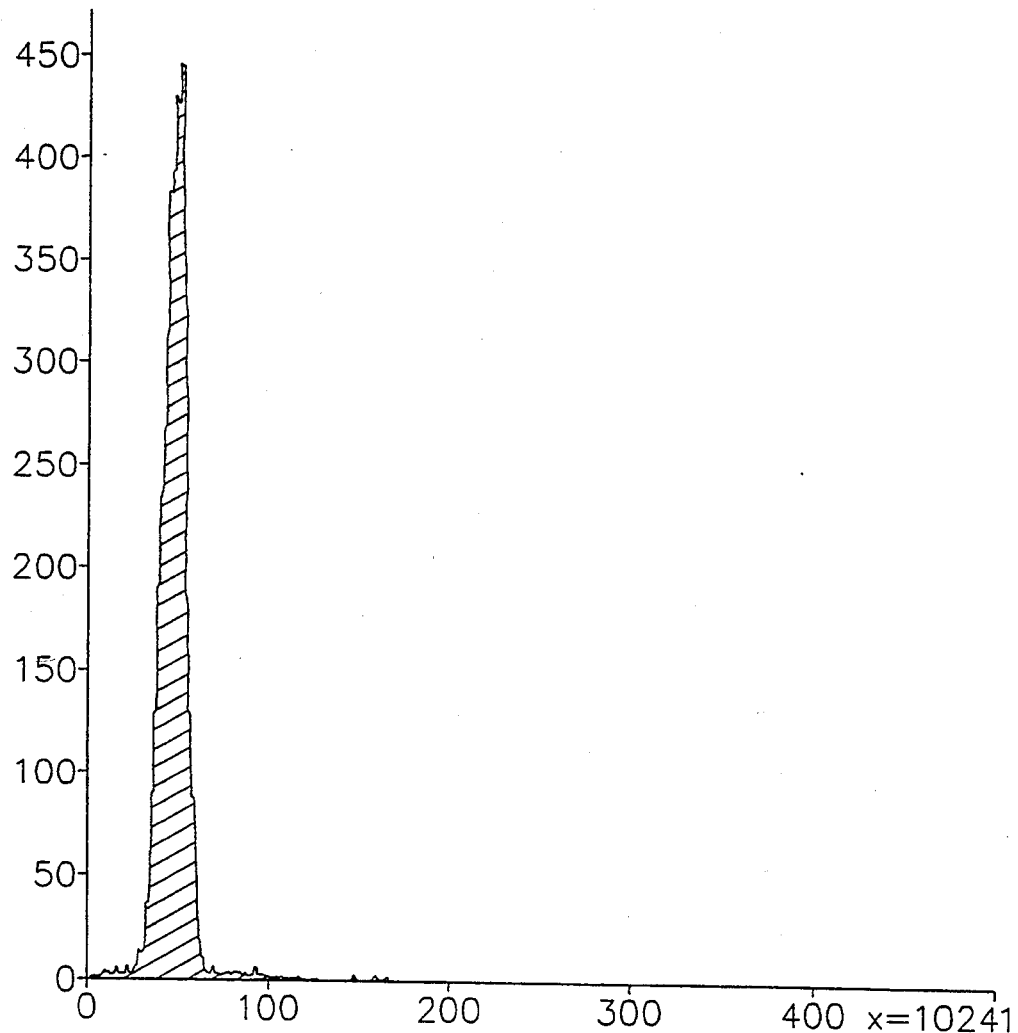

Covalent coupling of carboxylated fluorescent particles with anti-enterotoxin A rabbit polyclonal antibodies:

a—Preparation of beads (Fluoresbrite-Polysciences):
  0.5 mg of beads in 2.5% suspension in 4 ml of borate buffer ($10^{-2}$M boric acid +0.15M NaCl, pH 8.1);
  prepare a solution containing 80 µmoles of hexamethylene-diamine in 1 ml of borate buffer;
  add thereto the 4 ml of beads;
- add 0.05M carbodiimide;
- incubate overnight at 4° C.;
- wash with the borate buffer.

b—Preparation of the antibody:
- dialyse the antibodies against phosphate buffer 0.1M, pH 6;
- provide $\frac{2}{3}$antibodies per $\frac{1}{3}$of beads;
- add 200 μl of $NaIO_4$ 0.15M;
- incubate 3 hours at 4° C. in darkness;
- add glycerol to a final concentration of 0.015M;
- incubate 30 minutes at ambient temperature;
- dialyse against phosphate buffer pH 6;

c—Coupling proper:
- add the beads and the antibodies in the presence of 5 ml of borate buffer;
- incubate 16 hours at 4° C. with stirring;
- adjust the pH to 8.8;
- stabilise with $NaBH_4$ (5 ml in the test);
- incubate 5 hours at 4° C.;
- wash with 0.5% PBS-BSA 0.1% Tween.

Non-covalent coupling of carboxylated fluorescent particles with anti-enterotoxin A rabbit polyclonal antibodies:

a—In a glass tube:
- 100 μl of an antibody solution with 2.5 mg/ml;
- 100 μl of Glycine buffer (Meth. Enzymol. 74, 111);
- 5 μl of beads diluted to 1/10;

b—Stirring for 30 minutes at ambiant temperature;

c—Rinsing: 3 times in a 0.5% PBS-BSA—0.1% Tween buffer;

d—Take up again in 100 μPBS.

2) Detection of the substance sought:

a) a detection system such as prepared in 1) is used;

b) the detection system is mixed with a quantity of antigen; it is incubated 2 hours at 37° C. and the agglutinated and non-agglutinated beads are detected; the results are presented in Table I and in FIG. 1.

Table I, below, shows a comparative test between a negative control (beads coated with antibodies but absence of enterotoxin) for which 10.5% of agglutinated beads are obtained (FIG. 1 and column A of Table I) and a detection of enterotoxin A, by the method according to the invention, (FIG. 2 and column B of Table I), for which 85% of agglutinated beads are obtained, in the presence of a specimen containing 10 mg of enterotoxin A; the agglutination is proportional to the concentration of enterotoxin A within a given range of concentrations.

In FIGS. 1, 2 and 3, are shown as abscissae, the relative fluorescence measurement (channel) the number of the channel and as ordinate, the number of particles or of aggregates of particles per channel.

FIG. 1 shows the result obtained with latex beads coupled to antibodies (negative control) and corresponds to the results mentioned in Table I, column A.

FIG. 2 shows, in the form of a histogram, the results mentioned in Table I, column B.

FIG. 3 shows the result obtained with fluorescent latex beads not coupled to antibodies (other negative control) but in the presence of antigen. An agglutination of less than 2% is observed.

TABLE I

CARBOXYLATED 1.1 μm BEADS COUPLED WITH AN ANTI-ENTEROTOXIN A RABBIT POLYCLONAL ANTIBODY

| No of beads per clump | Channel | 1.1 μm BEADS + ANTIBODY A | | | 1.1 μm BEADS + ANTIBODY + 10 ng ENTEROTOXIN A | | |
|---|---|---|---|---|---|---|---|
| | | Event/Histo | Beads/Histo | % | Event/Histo | Beads/Histo | % |
| 1 | 5225 | 9475 | 9475 | 89,522 | 8312 | 8312 | 15,497 |
| 2 | 1125 | 466 | 932 | 8,8057 | 4198 | 8396 | 15,654 |
| 3 | 16875 | 59 | 177 | 1,6723 | 2714 | 8142 | 15,18 |
| 4 | 225 | | | | 1581 | 6324 | 11,791 |
| 5 | 28125 | | | | 1145 | 5725 | 10,674 |
| 6 | 3375 | | | | 660 | 3960 | 7,3832 |
| 7 | 39375 | | | | 495 | 3465 | 6,4603 |
| 8 | 450 | | | | 245 | 1960 | 3,6543 |
| 9 | 50625 | | | | 180 | 1620 | 3,0204 |
| 10 | 5625 | | | | 126 | 1260 | 2,3492 |
| 11 | 61875 | | | | 122 | 1342 | 2,5021 |
| 12 | 675 | | | | 69 | 828 | 1,5438 |
| 13 | 73125 | | | | 58 | 754 | 1,4058 |
| 14 | 7875 | | | | 33 | 462 | 0,8614 |
| 15 | 84375 | | | | 31 | 465 | 0,867 |
| 16 | 900 | | | | 11 | 176 | 0,3281 |
| 17 | 95625 | | | | 12 | 204 | 0,3603 |
| 18 | 10125 | | | | 13 | 240 | 0,4475 |
| 19 | 10688 | | | | | | |
| SUM | | 10000 | 10584 | 100 | 20005 | 53635 | 100 |

Table II, below, shows the results obtained with a negative control (beads coated with antibodies, but in the absence of corresponding antigen) under slightly different operational conditions (gentle stirring for 30 minutes only). In this case, 1.6% of agglutinated beads are obtained (background noise and interference very slight).

TABLE II

| Number of beads per clump | Channel | 1.1 μm BEADS + ANTIBODIES 30 MIN | | |
|---|---|---|---|---|
| | | Event/Histo | Beads/Histo | % |
| 1 | 56 | 10787 | 10787 | 98.395 |
| 2 | 112 | 88 | 176 | 1.6054 |
| 3 | 168 | | | |
| 4 | 224 | | | |
| 5 | 280 | | | |
| 6 | 336 | | | |
| 7 | 392 | | | |
| 8 | 448 | | | |
| 9 | 504 | | | |
| 10 | 560 | | | |
| 11 | 616 | | | |
| 12 | 672 | | | |
| 13 | 728 | | | |
| 14 | 784 | | | |
| 15 | 840 | | | |
| 16 | 896 | | | |
| 17 | 952 | | | |
| 18 | 1008 | | | |
| 19 | | | | |

TABLE II-continued

| | 1.1 μm BEADS + ANTIBODIES 30 MIN | | |
|---|---|---|---|
| Number of beads per clump | Channel | Event/Histo | Beads/Histo | % |
| SUM | | 10875 | 10963 | 100 |

EXAMPLE 2

Study of the stability of beads coated with suitable antibodies

Beads coated with anti-enterotoxin A rabbit polyclonal antibodies, such as described in Example 1, are used one week after their preparation; the results as shown in Table III are obtained:

in column A are shown the results relating to a negative control, beads coated with antibodies;
  in column B are shown the results concerning an enterotoxin A detection test, the amount of the latter being 10 ng; the reading of the result is performed after 20 minutes with gentle stirring;
  in column C are shown the results relating to an enterotoxin A detection test, the amount of the latter being 50 ng; the reading of the result is carried out after 20 minutes with gentle stirring;
  an inhibition of the agglutination of the beads in the case of excess antigen (50 ng against long) is observed: 51.3% of non-agglutinated beads against 42.7% of non-agglutinated beads is observed; the addition of free specific antibodies re-establishes the agglutination of the beads coated with antibodies which are saturated with antigen.

TABLE III

CARBOXYLATED 1.1 μm BEADS COUPLED WITH AN ANTI-ENTEROTOXIN A RABBIT POLYCLONAL ANTIBODY

| Number of beads per clump | Channel | A 1.1 μm BEADS + ANTIBODIES | | | B 1.1 μm BEADS + ANTIBODIES + 10 ng ENTEROTOXIN A 20 min | | | C 1.1 μm BEADS + ANTIBODIES + 50 ng ENTEROTOXIN A 20 min | | |
|---|---|---|---|---|---|---|---|---|---|---|
| | | Event/Histo | Beads/Histo | % | Event/Histo | Beads/Histo | % | Event/Histo | Beads/Histo | % |
| 1 | 56 | 7831 | 7831 | 92.119 | 11308 | 11308 | 42.7 | 11878 | 11878 | 51.29 |
| 2 | 112 | 158 | 316 | 3.717 | 2280 | 4560 | 17.22 | 1714 | 3428 | 14.80 |

TABLE III-continued

CARBOXYLATED 1.1 μm BEADS COUPLED WITH AN ANTI-ENTEROTOXIN A RABBIT POLYCLONAL ANTIBODY

| Number of beads per clump | Channel | A 1.1 μm BEADS + ANTIBODIES | | | B 1.1 μm BEADS + ANTIBODIES + 10 ng ENTEROTOXIN A 20 min | | | C 1.1 μm BEADS + ANTIBODIES + 50 ng ENTEROTOXIN A 20 min | | |
|---|---|---|---|---|---|---|---|---|---|---|
| | | Event/Histo | Beads/Histo | % | Event/Histo | Beads/Histo | % | Event/Histo | Beads/Histo | % |
| 3 | 168 | 118 | 354 | 4.164 | 777 | 2331 | 8.80 | 663 | 1989 | 8.58 |
| 4 | 224 | | | | 436 | 1744 | 6.58 | 313 | 1252 | 5.40 |
| 5 | 280 | | | | 239 | 1195 | 4.51 | 196 | 980 | 4.23 |
| 6 | 336 | | | | 163 | 978 | 3.69 | 113 | 678 | 2.92 |
| 7 | 392 | | | | 127 | 889 | 3.35 | 68 | 476 | 2.05 |
| 8 | 448 | | | | 80 | 640 | 2.41 | 52 | 416 | 1.79 |
| 9 | 504 | | | | 72 | 648 | 2.44 | 44 | 396 | 1.71 |
| 10 | 560 | | | | 41 | 410 | 1.54 | 30 | 300 | 1.29 |
| 11 | 616 | | | | 41 | 451 | 1.70 | 26 | 286 | 1.23 |
| 12 | 672 | | | | 26 | 312 | 1.17 | 22 | 264 | 1.14 |
| 13 | 728 | | | | 16 | 208 | 0.78 | 12 | 156 | 0.67 |
| 14 | 784 | | | | 18 | 252 | 0.95 | 10 | 140 | 0.60 |
| 15 | 840 | | | | 9 | 135 | 0.51 | 10 | 150 | 0.64 |
| 16 | 896 | | | | 8 | 128 | 0.48 | 11 | 176 | 0.76 |
| 17 | 952 | | | | 14 | 238 | 0.89 | 8 | 136 | 0.58 |
| 18 | 1008 | | | | 3 | 54 | 0.20 | 3 | 54 | 0.23 |
| SUM | | 8107 | 8501 | 100 | 15658 | 26481 | 100 | 15173 | 23155 | 100 |

In the following examples, by green fluorescent beads is meant beads marked with coumarin and by red fluorescent beads, beads marked with phycoerythrin R.

EXAMPLE 3

Analysis of the immune protection of the pregnant woman against toxoplasmosis

Fluorescent beads coated with toxoplasmic antigen as well as fluorescent beads coated with anti-IgG antibodies and beads covered with anti-IgM antibodies as in Example 1 (1a) are prepared.

The objective consisted of seeking simultaneously the presence of anti-toxoplasmin antibodies of isotypes IgG and IgM. Green fluorescent beads were coated with toxoplasmic antigen and were then incubated with the blood specimen in the presence of green beads coated with anti-IgG antibodies and with red beads coated with anti-IgM antibodies. The proportion of green/green doublets on the one hand and green/red on the other hand enables the searching and quantifying simultaneously of IgG and IgM antibodies. The aggregates with three beads or more were analysed for their red and green components. In addition, a reference curve was established.

EXAMPLE 4

Rapid determination of isomers or of denaturated epitopes

Fluorescent beads coated with a suitable antiligand as in Example 1 are prepared.

A monoclonal antibody common to all isomers or recognising all native and denaturated forms of a protein coats green beads. A specific monoclonal antibody of each modified form is coupled to beads either green or red. The search for green/green and green/red aggregates gives simultaneously the total amount of antigen and the proportion of two (or more, if several bead colours are selected) forms of the molecule.

EXAMPLE 5

Determination of haptens by inhibition of agglutination.

Beads coated with the appropriate antiligand are prepared as in Example 1.

Fluorescent beads are coated with a derivative of the hapten, for example aflatoxin-poly-L-lysine. The mixture of these beads with a homogeneous population of beads coated with an anti-aflatoxin monoclonal antibody will give agglutination. The possible presence of free aflatoxin in a food specimen will cause, on its addition to the mixture of beads, an inhibition of agglutination by competition in its fixation to the monoclonal antibody.

EXAMPLE 6

Search, analysis and determination of complex carbohydrates

The fixation of lectins of different specificities (for example concanavaline A for $\alpha$-D-glucosyl and agglutinin of wheat germ for $[\beta$-N-acetylglucosaminyl$]_n$ or sialic acids) on beads of different colors, according to the procedure of Example 1, enables the determination of whether the sugars recognized by these lectins are borne by the same molecule (agglutination) or by different molecules (no agglutination); this constitutes also a tool for the determination of structures: there are known to date in fact several tens of different lectins.

EXAMPLE 7

Search for very low concentrations of antibodies (amplification of agglutination)

A very small amount of antibody cannot cause spontaneous agglutination. This is the case in the determination of specific IgG's in allergy diagnosis.

Different allergens are coupled with beads of different sizes and/or colors, according to the procedure of Example 1. The mixture of this bead population with the biological specimen will cause the fixation of the specific antibodies to the corresponding allergens. Amplification of agglutination is then obtained by adding a bivalent specific anti-IgE antibody which will associate two IgE molecules and hence two beads.

This test can also be used for the search for and determination of IgM, IgA and IgD.

EXAMPLE 8

Search for specific sequences of nucleic acids

Two (or more) nucleic probes hybridizing with complementary sequences on a same gene are coupled to beads of different colors, according to the procedure of Example 1.

The nucleic material, freed from the cells, is placed in the presence of different populations of fluorescent beads under hybridization conditions.

The search for aggregates is done by flow cytometry, by image analysis or by laser sweep. The presence of aggregates constituted from beads of the same color indicates the presence of repetitive sequences on the same gene or the same chromosome whereas aggregates constituted from beads of different colors indicates the complementary distance of two (or more) of the specific sequences sought.

Thus as is apparent from the foregoing, the invention is in no way limited to those of its types of practice, embodiments and uses which have just been described more explicitly; it encompasses, on the contrary, all modifications which may come to the spirit of the technician skilled in the art, without departing from either the framework, or the scope of the present invention.

I claim:

1. A method for determining the presence or absence of each of a predetermined number of different ligands selected from one or two ligands in a liquid, semi-liquid or pasty specimen, by a direct or indirect agglutination, or an agglutination inhibition method by competition, comprising the steps:
   contacting the specimen with a predetermined number of homogeneous populations of fluorescent beads, each population having a specific fluorescence and having one or more predetermined antiligands fixed to their surface, said predetermined number of populations being equal to said predetermined number of ligands;
   analyzing said specimen containing said beads using a measuring means capable of discriminating between the specific fluorescence of said beads for each ligand, said measuring means being selected from the group consisting of a flow cytometer, an image analyzer and a laser sweep system;
   determining in response to said analyzing step the number of non-agglutinated beads, the number of agglutinated beads, the number of bead aggregates and for each aggregate, the number of the beads it comprises, by absolute measurement of the intensity and the fluorescence wavelength of each particle or aggregate of particles, one by one; and
   correlating the information determined in said determining step with the presence or absence in said specimen, of each of said different ligands to thereby enable the simultaneous determination of a plurality of ligands using a single bead contacting step.

2. The method according to claim 1, wherein said beads comprise at least two predetermined antiligands fixed to their surface.

3. The method according to claim 1, wherein said beads have a diameter of between 0.05 µm and 10 µm.

4. The method according to claim 1, wherein said antiligand is selected from the group consisting of antigens, antibodies, receptors, lectins, proteins of type A or G, and avidin, said antiligand being specific to one or more of said predetermined number of different ligands.

5. The method according to claim 4, wherein the antibodies are monoclonal antibodies.

6. The method according to claim 4, wherein the antibodies are polyclonal antibodies.

7. The method according to claim 1 wherein said correlating step is conducted in a manner to determine quantitative values for each of said ligands.

8. A method for determining the presence or absence of each two different ligands in a liquid, semi-liquid or pasty specimen, by a direct or indirect agglutination, or an agglutination inhibition method by competition, comprising the steps of:
   contacting the specimen with a predetermined plurality of homogeneous populations of fluorescent beads, each population having a specific fluorescence and having one or more predetermined antiligands fixed to their surface, said predetermined plurality of populations being two populations;
   analyzing said specimen containing said beads using a measuring means capable of discriminating between the specific fluorescence of said beads for each ligand, said measuring means being selected from the group consisting of a flow cytometer, an image analyzer and a laser sweep system;
   determining in response to said analyzing step, the number of non-agglutinated beads, the number of agglutinated beads, the number of bead aggregates and for each aggregate, the number of the beads it comprises and the population type or types of beads it comprises, by absolute measurement of the intensity and the fluorescence wavelength of each particle or aggregate of particles, one by one; and
   correlating the information determined in said determining step with the presence or absence in said specimen of each of said different ligands to thereby enable the simultaneous determination of a plurality of ligands using a single bead contacting step.

9. The method according to claim 8 wherein the beads in at least one of said homogenous populations of beads comprise at least two antiligands affixed to their surface.

10. The method according to claim 8 wherein said beads have a diameter of between 0.05 µm and 10 µm.

11. The method according to claim 8 wherein the antiligands fixed to the surface of said beads are specific to one or more of said predetermined plurality of different ligands and are selected from the group consisting of antigens, antibodies, receptors, lectins, proteins of type A or G, or avidin.

12. The method according to claim 11 wherein the antibodies are monoclonal antibodies.

13. The method according to claim 11 wherein the antibodies are polyclonal antibodies.

14. The method according to claim 8 wherein said correlating step is conducted in a manner to determine quantitative values for each of said ligands.

* * * * *